US005801241A

United States Patent [19]
Lim et al.

[11] Patent Number: 5,801,241
[45] Date of Patent: Sep. 1, 1998

[54] CYCLOHEXANONE EXTRACTION OF 3-HYDROXYMETHYLCEPHALOSPORINS

[75] Inventors: Gary M. F. Lim; John M. Roubie, both of Onondaga, N.Y.; Vicki H. Audia, Plainsboro, N.J.

[73] Assignee: Bristol-Myers Squibb Company, Princeton, N.J.

[21] Appl. No.: 896,377

[22] Filed: Jul. 18, 1997

Related U.S. Application Data

[60] Provisional application No. 60/022,372 Jul. 29, 1996 and provisional application No. 60/030,214 Nov. 5, 1996.

[51] Int. Cl.$^6$ ............................................. C07D 501/28
[52] U.S. Cl. ................................................ 540/230
[58] Field of Search .................................... 540/230

[56] References Cited

U.S. PATENT DOCUMENTS

| | | | |
|---|---|---|---|
| 3,573,296 | 3/1971 | Johnson et al. | 260/243 |
| 3,830,809 | 8/1974 | Brooks, Jr. | 260/243 |
| 3,835,129 | 9/1974 | Wild | 260/243 |
| 3,980,644 | 9/1976 | Lunn | 424/246 |
| 3,986,644 | 10/1976 | Grogan et al. | 222/207 |
| 4,168,375 | 9/1979 | Andrisano et al. | 544/20 |
| 4,533,632 | 8/1985 | Smith et al. | 435/47 |
| 4,908,444 | 3/1990 | Naito et al. | 540/230 |
| 5,221,739 | 6/1993 | Wildfeuer | 540/230 |
| 5,424,196 | 6/1995 | Cambiaghi et al. | 435/51 |

FOREIGN PATENT DOCUMENTS 2060610A  5/1981  European Pat. Off. .

OTHER PUBLICATIONS

M.E. Wildfeuer, "Aqueous Acetylation of Desacetyl Glutaryl 7–Amino–Cephalosporanic Acid (7 ACA) and Speculation on the Origin of Cephalosporin C in Fermentation Broth," Journal of Antibiotics, 47(1), pp. 64–71, 1994.

*Primary Examiner*—Mark L. Berch
*Attorney, Agent, or Firm*—David M. Morse

[57] ABSTRACT

The cephalosporin intermediates, desacetyl 7-glutaryl ACA and desacetyl cephalosporin D, are obtained in the form of a concentrated aqueous solution from an aqueous solution containing said intermediates in less concentrated form by solvent extraction using cyclohexanone followed by back-extraction into water. The concentrated aqueous solution of intermediate is in a form which can be used for economical production of 7-ACA using known procedures.

6 Claims, No Drawings

CYCLOHEXANONE EXTRACTION OF 3-HYDROXYMETHYLCEPHALOSPORINS

This application claims the benefit of U.S. Provisional application Ser. No. 60/022,372, filed Jul. 29, 1996 and U.S. Provisional application Ser. No. 60/030,214, filed Nov. 5, 1996.

FIELD OF THE INVENTION

This invention relates to an improved process for obtaining concentrated aqueous solutions of 3-hydroxymethylcephalosporin compounds from aqueous fermentation broths. More particularly, it relates to the cyclohexanone extraction of certain 3-hydroxymethylcephalosporin intermediates from aqueous fermentation broths followed by back-extraction into an aqueous solution to provide a concentrated aqueous solution of the desired 3-hydroxymethylcephalosporin intermediate.

BACKGROUND OF THE INVENTION

7-Aminocephalosporanic acid (7-ACA) and various derivatives thereof are known important intermediates in the production of antibiotics of the cephalosporin class. The 7-ACA and derivatives thereof having various 3-substituents may be obtained from fermentation-derived cephalosporin C by known processes. For example, the conversion of cephalosporin C to 7-ACA can be carried out by known chemical and enzymatic processes.

U.S. patent application Ser. No. 4,533,632 describes a process for obtaining desacetyl cephalosporin C in an aqueous fermentation broth and reports that this product has significant advantages over cephalosporin C in the production of cephalosporin derivatives.

Other references such as U.S. Pat. No. 5,424,196 disclose enzymatic processes for converting desacetyl cephalosporin C produced in an aqueous fermentation broth to desacetyl 7-glutaryl ACA containing a 3-hydroxymethyl substituent.

Takeda in U.S. Pat. No. 4,908,444 and Lilly in U.S. Pat. No. 5,221,739 and *J. Antibiotics* 47(1):64–71, 1994, disclose a process for acetylating desacetyl 7-glutaryl ACA in aqueous solution with acetic anhydride to produce 7-glutaryl ACA which can then be enzymatically hydrolyzed to 7-ACA in high yield.

Despite the progress which has been made toward an enzymatic 7-ACA process which would use desacetyl 7-glutaryl ACA produced from an aqueous fermentation broth, such a process is still not commercially feasible. One serious problem is that the desacetyl 7-glutaryl ACA is obtained in the fermentation broth in low concentrations (~1–3%) and cannot be economically acetylated at these concentrations by the prior art methods. It is reported, for example in the above-mentioned Lilly patent and *J. Antibiotics* paper, that the acetylation reaction works best at high concentrations of desacetyl 7-glutaryl ACA, preferably above 10%. So far it has not been possible to obtain from desacetyl cephalosporin C fermentation broths an adequately concentrated (≧10% weight/volume) aqueous solution of desacetyl 7-glutaryl ACA to allow the aqueous acetylation step to be commercially feasible.

A related cephalosporin C derivative, N-carbisobutoxycephalosporin C, having the formula

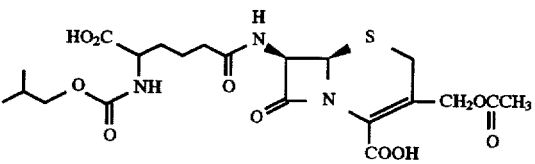

and its bis-dicyclohexylamine salt are disclosed in U.S. Pat. Nos. 3,573,296 and 3,830,809 as useful intermedites in the chemical synthesis of 7-ACA. The intermediate N-carbisobutoxycephalosporin C is referred to herein and in the claims as "cephalosporin D". In order to take advantage of improvements in high titer desacetyl cephalosporin C fermentation (see, for example, U.S. Pat. No. 4,533,632) for production of 7-ACA using cephalosporin D, it is necessary to first convert the desacetyl cephalosporin C produced in the broth to desacetyl cephalosporin D of the formula

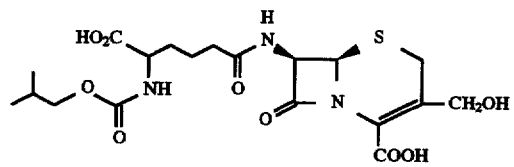

by acylation with isobutylchloroformate according the general procedures of U.S. Pat. No. 3,573,296. The so-produced desacetyl cephalosporin D then needs to be acetylated with acetic anhydride according to the general procedures of U.S. Pat. Nos. 4,908,444 and 5,221,739 to give cephalosporin D. This product can be conveniently isolated in the form of the bisdicyclohexylamine salt as disclosed in U.S. Pat. No. 3,830,809.

As in the case of acetylation of desacetyl 7-glutaryl ACA discussed above, however, high concentrations (≧10% weight/volume) of the desacetyl cephalosporin D are required for the acetylation step to be costeffective. Also, as in the case of desacetyl 7-glutaryl ACA, there have been no practical ways to obtain the desacetyl cephalosporin D from fermentation broths in such high concentrations.

A variety of organic solvents have been used in the extraction of cephalosporin products from aqueous fermentation broths, e.g. n-butyl acetate, methylene chloride, methylisobutyl ketone, chloroform and ethyl acetate. U.S. Pat. No. 3,835,129 mentions that cyclohexanone was considered to be a good N-acyl cephalosporin C extraction solvent, but that it presented emulsion problems when used in large scale operations. U.S. Pat. No. 4,168,375 discloses cyclohexanone in a list of possible extraction solvents for sulfonamide derivatives of cephalosporin C, but does not mention extraction of 3-hydroxymethylcephalosporins. Cyclohexanone is used to extract certain cephalosporin C phosphorous amide derivatives in U.S. Pat. No. 3,980,644, but again no mention is made of 3-hydroxymethylcephalosporins.

The present inventors have found that 3-hydroxymethylcephalosporins such as desacetyl 7-glutaryl ACA and desacetyl cephalosporin D are difficult or impossible to extract with common organic solvents employed with other cephalosporin compounds such as N-blocked cephalosporin C, but that use of cyclohexanone as the extracting solvent according to the process of the present invention allows a sufficiently concentrated aqueous solution of desacetyl 7-glutaryl ACA or desacetyl cephalosporin D to be obtained from the fermentation broth to economically practice the above-described aqueous acetylation step to give 7-glutaryl ACA and cephalosporin D which can then be converted to 7-ACA by known procedures.

SUMMARY OF THE INVENTION

The present invention provides a process for preparing concentrated ($\geq 10\%$ weight/volume) aqueous solutions of desacetyl 7-glutaryl ACA or desacetyl cephalosporin D from an aqueous solution, preferably an aqueous fermentation broth and most preferably a processed fermentation broth, containing the desacetyl 7-glutaryl ACA or desacetyl cephalosporin D in lower concentration, which comprises the steps of:

(a) providing an aqueous solution, preferably a fermentation broth and most preferably a processed fermentation broth, containing desacetyl 7-glutaryl ACA or desacetyl cephalosporin D;

(b) contacting the solution with cyclohexanone at a pH of from about 1.5 to about 3 so as to extract the desacetyl 7-glutaryl ACA or desacetyl cephalosporin D into the cyclohexanone solvent phase;

(c) separating the cyclohexanone solvent phase from the aqueous phase;

(d) contacting the cyclohexanone phase with water at a pH of from about 5 to about 7.5; and (e) separating the aqueous phase containing the desired concentrated solution of desacetyl 7-glutaryl ACA or desacetyl cephalosporin D.

DETAILED DESCRIPTION OF THE INVENTION

As indicated above, carrying out the enzymatic process for preparing 7-ACA from desacetyl cephalosporin C on a commercial scale requires economical yields in the key acetylation step, i.e. the acetic anhydride aqueous acetylation of desacetyl 7-glutaryl ACA to 7-glutaryl ACA. Economical yields in this step are dependent on using concentrated ($\geq 10\%$ weight/volume) aqueous solutions of the desacetyl 7-glutaryl ACA starting material. When this material is obtained from a fermentation broth, however, it is present in the broth at a much lower concentration, on the order of ~1–3% weight/volume, so it is necessary to extract the desacetyl 7-glutaryl ACA from the fermentation broth and concentrate it for the acetylation step to be practical and competitive with chemical synthesis methods for preparing 7-ACA.

Similarly, in employing the known intermediate, cephalosporin D, to obtain 7-ACA by the traditional chemical synthesis route, it is highly desirable to take advantage of recent improvements in high titer desacetyl cephalosporin C fermentation by converting the desacetyl cephalosporin C produced during fermentation to desacetyl cephalosporin D and then extracting this material from the aqueous broth in high concentrations ($\geq 10\%$ weight/volume) so as to result in the aqueous acetylation reaction step with acetic anhydride giving the cephalosporin D product in high yield.

In a preferred embodiment the process of the present invention uses as the starting material a processed fermentation broth containing desacetyl 7-glutaryl ACA or desacetyl cephalosporin D. As used herein, the term "processed fermentation broth" means a desacetyl cephalosporin C fermentation broth which has been converted by enzymatic processes, e.g. those disclosed in U.S. Pat. No. 5,424,196, to a broth containing desacetyl 7-glutaryl ACA or which has been converted chemically as by acylation with isobutylchloroformate to a broth containing desacetyl cephalosporin D. The desacetyl 7-glutaryl ACA or desacetyl cephalosporin D must be present in the processed broth in a recoverable amount and is generally present in a fairly low concentration of from about 1–3% (weight/volume) The processed broth can be used directly or after being subjected to purification steps such as pH adjustment and filtration. The processed broth may also be subjected to treatment by one or more resin columns to further purify it; this latter aqueous medium is sometimes referred to as "resin eluate".

The aqueous solution, preferably a processed fermentation broth, is contacted with cyclohexanone as the extraction solvent and stirred or otherwise vigorously mixed with the broth to give two solvent phases. Before or during extraction with the cyclohexanone, the solution or mixture is adjusted to a pH of from about 1.5 to about 3, preferably about 2, with an inorganic acid such as sulfuric acid, nitric acid or hydrochloric acid. The temperature for the cyclohexanone extraction step is not critical, but it is preferred to do the extraction at a temperature in the range of from about 0° C. to about room temperature, most preferably in the range of about 5°–10° C. Following the extraction, the aqueous phase may be extracted again with cyclohexanone to obtain additional amounts of desacetyl 7-glutaryl ACA or desacetyl cephalosporin D and the cyclohexanone layers combined. The cyclohexanone extraction results in a high percentage, generally over 90%, of the desacetyl 7-glutaryl ACA or desacetyl cephalosporin D being extracted from the broth.

Since the acetylation step to produce 7-glutaryl ACA or cephalosporin D is done under aqueous conditions, it is necessary to backextract the cyclohexanone layer containing the desacetyl 7-glutaryl ACA or desacetyl cephalosporin D with water to get the desired concentrated aqueous solution. The cyclohexanone phase is separated from the aqueous phase and contacted with water at a pH in the range of from about 5 to about 7.5 to again give two solvent phases, this time the aqueous phase containing the desacetyl 7-glutaryl ACA or desacetyl cephalosporin D. The solvent phases are separated to give the desired aqueous solution. The base used for pH adjustment in this step is not critical, but it is preferred to use an acetate buffer such as sodium or potassium acetate. The temperature for this extraction step can be the same as that used for the cyclohexanone extraction. The back-extraction with water gives high yields, again over 90% of the desacetyl 7-glutaryl ACA or desacetyl cephalosporin D being recovered in the aqueous phase.

The process of the present invention provides aqueous desacetyl 7-glutaryl ACA or desacetyl cephalosporin D solutions in concentrations of $\geq 10\%$. Concentrations in the range of 10–20% weight/volume are achievable, with 15% concentrations being easily obtained and preferred for the subsequent acetylation step. The extraction and subsequent back-extraction process in combination allow for removal of fermentation salts as well as concentration of the desacetyl 7-glutaryl ACA or desacetyl cephalosporin D.

As mentioned above, cyclohexanone was found to be a unique solvent for extraction of 3-hydroxymethylcephalosporins such as desacetyl 7-glutaryl ACA and desacetyl cephalosporin D. Common organic solvents used to extract other cephalosporin intermediates such as N-blocked cephalosporin C from fermentation broths are not useful for 3-hydroxymethylcephalosporins. To illustrate this, the following tables show the percentage of desacetyl 7-glutaryl ACA and desacetyl cephalosporin D extracted using a variety of industrial solvents.

| Extractions of Desacetyl 7-Glutaryl ACA (from processed fermentation broth) | | |
| --- | --- | --- |
| Solvent | % Extracted | |
| methylisobutyl ketone | 5 | |
| n-butyl acetate | 1 | |
| n-butyl acetate/n-butanol (20%) | 17 | |
| n-butanol | 52.5 | |
| ethyl acetate | 8.4 | |
| cyclohexanone | 72.5 | (98% after 3 extractions) |

| Extractions of Desacetyl Cephalosporin D (from processed fermentation broth) | |
| --- | --- |
| Solvent | % Extracted |
| methylisobutyl ketone | 45.6 |
| n-butyl acetate | 13.4 |
| n-butyl acetate/n-butanol (6%) | 67 |
| ethyl acetate | 75.8 |
| cyclohexanone | 88.4 |

Cyclohexanone was clearly the best extraction solvent, although in the case of desacetylcephalosporin D, ethyl acetate and n-butylacetate with added butanol extracted well. Solvent recovery for ethyl acetate is expected to be poor, however, because of the easy hydrolysis of the ethyl acetate to ethanol and acetic acid. The presence of alcohol, such as butanol, in the back extract can interfere in the subsequent acetylation step. It was also found that lactonization of the desacetyl 7-glutaryl ACA was significantly reduced using cyclohexanone as the extraction solvent. The overall extraction/back-extraction process of the present invention gives a greater than 10-fold concentration of the desacetyl 7-glutaryl ACA or desacetyl cephalosporin D and the resulting concentrated aqueous solution is compatible with the aqueous acetylation reaction process without the need for further processing.

The following examples are used to illustrate the invention.

EXAMPLE 1

A 2.7% desacetyl 7-glutaryl ACA aqueous solution (1180 ml) and cyclohexanone (1180 ml) were stirred and 6N HCl was added to adjust the mixture to pH 2.0. The mixture was transferred to a separatory funnel and extracted. Layers were separated and cyclohexanone layer was retained. The aqueous layer was extracted with fresh cyclohexanone (2×1000 ml).

Combined cyclohexanone layers (3220 ml) were evaluated and a 0.928% solution was obtained. The desacetyl 7-glutaryl ACA was extracted with 92% efficiency. Cyclohexanone extract (3215 ml) containing desacetyl 7-glutaryl ACA (0.928%) was back extracted with 4.0M sodium acetate (NaOAc) (90.0 ml). Initial pH of the mixture rose from pH 2.4 to pH 5.87. Separation of the layers afforded an aqueous layer (151.5 ml) at an 18.1% concentration. Back extraction of desacetyl 7-glutaryl ACA was accomplished with 92% efficiency. Overall efficiency of desacetyl 7-glutaryl ACA extraction was 84%.

EXAMPLE 2

A 2.48% desacetyl 7-glutaryl ACA aqueous solution (910 ml) and cyclohexanone (910 ml) were stirred and 6N HCl was added to adjust the mixture from pH 7.2 to pH 2.0. The mixture was transferred to a separatory funnel and extracted. Layers were separated and cyclohexanone layer was retained. The aqueous layer was extracted with fresh cyclohexanone (2×910 ml). Combined cyclohexanone layers (2825 ml) were evaluated and a 0.77% solution was obtained. The desacetyl 7-glutaryl ACA was extracted with 96% efficiency. Cyclohexanone extract (2822 ml) containing desacetyl 7-glutaryl ACA (0.77%) was back extracted with 4.8M potassium acetate (KOAc) (60.0 ml). Initial pH of the mixture rose from pH 2.5 to pH 6.45. Separation of the layers afforded an aqueous layer (122.5 ml) (79%) at a 14.1% concentration. Back extraction with 1.0M KOAc (2×7.0 ml) afforded combined aqueous layers (18.2 ml) (7.6%). Back extraction of desacetyl 7-glutaryl ACA was accomplished with 87.6% efficiency. Overall efficiency of desacetyl 7-glutaryl ACA extraction was 84%.

EXAMPLE 3

Laboratory Scale Using Oxidized UF (Ultrafilter) Permeate Containing Desacetyl 7-Glutaryl ACA Solution: Using a DeLaval separator, filtered fermentation broth (10.19 L) containing desacetyl 7-glutaryl ACA (2.41%) was extracted at pH 2.0 with cyclohexanone (10.19 L). Each extraction was carried out on 1.9 L scale. Fresh permeate was extracted with rich cyclohexanone from the previous extraction to simulate a continuous extraction. A portion of the rich cyclohexanone (3830 ml) from the final solutions (1.18%) was back extracted with 4.0M NaOAc (150 ml) to afford an aqueous solution of desacetyl 7-glutaryl ACA (250 ml) (16.3%). Back extraction was accomplished in 90% efficiency.

EXAMPLE 4

A. Separatory Funnel Extraction

A solution of desacetyl cephalosporin D (17.88 g, 37.76 mmol, 1.9 L) was stirred (5° C.) with cyclohexanone (945 ml). The solution was adjusted from pH 7.18 to pH 2.27 with hydrochloric acid (6N, 86.0 ml). The two phase mixture was stirred for five minutes and pH 2.18 was observed. The mixture was transferred to a separatory funnel and the layers were separated. A small amount of a white emulsion was removed by filtration. The cyclohexanone layer (750 ml) and the aqueous layer (2195 ml) were sampled for HPLC analysis. Desacetyl Ceph D in cyclohexanone (18.5 g/L) was obtained in 77.5% yield. The aqueous solution contained the remaining desacetyl Ceph D (0.76 g/L, 9.4%). The material balance was 86.9%.

B. Extraction with DeLaval Separator

For ease of handling, the desacetyl cephalosporin D solution (4.025 L) was split into two portions. A solution of desacetyl cephalosporin D (17.36 g, 36.66 mmol, 2.0 L) was stirred (5° C.) with cyclohexanone (1.0 L). The solution was adjusted from pH 7.7 to pH 2.5 with hydrochloric acid (6N, 78.0 ml). The two phase mixture was stirred for five minutes. A solution of desacetyl cephalosporin D (17.58 g, 37.13 mmol, 2.025 L) was stirred (5° C.) with cyclohexanone (1.0 L). The solution was adjusted from pH 7.86 to pH 2.57 with hydrochloric acid (6N, 90.0 ml). The two phase mixture was stirred for five minutes. Both mixtures were transferred to a DeLaval Separator to separate the organic from the aqueous. A small amount of a white solids was present in the cyclohexanone layer. The cyclohexanone layer (1710 ml) and the aqueous layer (4020 ml) were sampled for HPLC analysis. Desacetyl cephalosporin D in cyclohexanone (17.92 g/L) was obtained in 87.7% yield. The aqueous solution contained the remaining desacetyl cephalosporin D (0.86 g/L, 9.9%). The material balance was 97.6%.

C. Back-Extraction into Water

A solution of desacetyl cephalosporin D in cyclohexanone (13.86 g, 29.27 mmol, 750 ml) was stirred (10° C.) with sodium acetate (2.0M, 124 ml). The solution was stirred and the pH increased from pH 2.13 to pH 5.77 (35 minutes). The solution was transferred to a separatory funnel and separated. The aqueous layer (170 ml) and the cyclohexanone layer (690 ml) were sampled for HPLC analysis. Desacetyl cephalosporin D (75.4 g/L) in an aqueous buffer solution was obtained in 92.5% yield. The cyclohexanone solution contained residual desacetyl cephalosporin D (0.46 g/L, 2.3%). The material balance was 94.8%.

We claim:

1. A process for preparing a concentrated ($\geq$10% weight/volume) aqueous solution of desacetyl 7-glutaryl ACA from an aqueous solution containing the desacetyl 7-glutaryl ACA in lower concentration, which comprises the steps of:

(a) providing an aqueous solution containing desacetyl 7-glutaryl ACA;

(b) contacting the solution with cyclohexanone at a pH of from about 1.5 to about 3 so as to extract the desacetyl 7-glutaryl ACA into the cyclohexanone solvent phase;

(c) separating the cyclohexanone solvent phase from the aqueous phase;

(d) contacting the cyclohexanone phase with water at a pH of from about 5 to about 7.5; and (e) separating the aqueous phase containing the desired concentrated solution of desacetyl 7-glutaryl ACA.

2. The process of claim 1 wherein the aqueous solution in Step (a) is a processed fermentation broth.

3. The process of claim 1 or claim 2 wherein Step(d) includes use of an acetate buffer.

4. A process for preparing a concentrated ($\geq$10% weight/volume) aqueous solution of desacetyl cephalosporin D from an aqueous solution containing the desacetyl cephalosporin D in lower concentration, which comprises the steps of (a) providing an aqueous solution containing desacetyl cephalosporin D;

(b) contacting the solution with cyclohexanone at a pH of from about 1.5 to about 3 so as to extract the desacetyl cephalosporin D into the cyclohexanone solvent phase;

(c) separating the cyclohexanone solvent phase from the aqueous phase;

(d) contacting the cyclohexanone phase with water at a pH of from about 5 to about 7.5; and (e) separating the aqueous phase containing the desired concentrated solution of desacetyl cephalosporin D.

5. The process of claim 4 wherein the aqueous solution in step (a) is a processed fermentation broth.

6. The process of claim 4 or claim 5 wherein step (d) includes use of an acetate buffer.

* * * * *